United States Patent
Chiu et al.

[11] Patent Number: 5,344,639
[45] Date of Patent: Sep. 6, 1994

[54] CONTRAST AGENT FOR NMR IMAGING COMPRISING PEPTIDE STRUCTURES

[75] Inventors: Kwok W. Chiu; Wassif Hussain; John R. Thornback, all of Uccle, Belgium

[73] Assignee: Medgenix Group S.A., Liege, Belgium

[21] Appl. No.: 719,715

[22] Filed: Jun. 26, 1991

[30] Foreign Application Priority Data

Jun. 26, 1990 [FR] France .................. 90 08009

[51] Int. Cl.$^5$ .............. A61B 5/055; C07C 229/00
[52] U.S. Cl. .................. 424/9; 562/565; 436/173; 128/653.4; 534/16; 556/50; 556/63; 556/107; 556/116; 556/134; 556/148
[58] Field of Search ............ 424/9; 562/565; 436/173; 128/653.4, 654; 556/50, 63, 107, 116, 134, 148; 534/16

[56] References Cited

U.S. PATENT DOCUMENTS

| | | | |
|---|---|---|---|
| 2,683,740 | 7/1954 | Worrall | 562/565 |
| 3,424,790 | 1/1969 | Bond | 260/534 |
| 4,584,121 | 4/1986 | Blaschke et al. | 252/106 |

FOREIGN PATENT DOCUMENTS

0299795  1/1989  European Pat. Off. .

Primary Examiner—Gary E. Hollinden
Attorney, Agent, or Firm—Wegner, Cantor, Mueller & Player

[57] ABSTRACT

The present invention relates to a contrast agent for NMR imaging constituted by a complex between a chelating agent and paramagnetic metal cations, wherein said complex corresponds to the formula I:

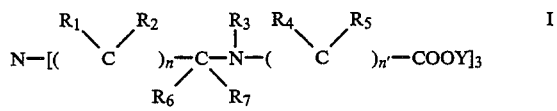

or a physiologically acceptable salt of this complex, in which formula:

n and n' are whole numbers from 1 to 4

$R_1$-$R_7$ are selected from among H, a halogen, alkyl, alkoxy, aryl, alkenyl, and cycloalkyl groups; with the alkyl groups being optionally substituted by halogen, alkoxy, alkyl, nitrile, nitro or amino; >C($R_6$, $R_7$) can in addition represent >C=O;

the three substituents Y are identical or different and represent H or an ionic equivalent of a divalent or trivalent paramagnetic metal cation or of a physiologically acceptable cation derived from an inorganic or organic base, with the condition that at least two of the substituents Y represent ionic equivalents of paramagnetic metal cations.

12 Claims, 1 Drawing Sheet

CONTRAST AGENT FOR NMR IMAGING COMPRISING PEPTIDE STRUCTURES

The present invention relates to contrast agents for NMR imaging constituted from a complex between a chelating agent and paramagnetic metal cations. The present invention relates also to chelating agents of a peptide structure which can form metal complexes as well as processes for the preparation of said contrast agents or chelating agents.

It has long been known that it is possible to use in the field of magnetic resonance imaging MRI, paramagnetic ions to facilitate the relaxation of the spin of certain atomic nuclei (Bloch F., Hancen W. M. and Packard N., Phys. Rev. 1946, 70, 474–485). In order that the phenomenon of NMR may be observable, the specimen must contain a large number of nuclei possessing a magnetic moment; this is the case of the hydrogen atom $^1H$ (protons of water), of phosphorus $^{31}P$ and of carbon $^{13}C$. In MRI, the spins of the atomic nuclei of the tissue under examination are oriented in a certain direction by means of a principal magnetic field. This orientation is then disturbed by application of an electromagnetic field of predetermined frequency (excitation process). When the second field is interrupted, the energy absorbed by the material during the excitation process is restituted by the nuclei whose magnetic moment will again align itself with the direction of the principal magnetic field. The energy emitted, called precession energy decreases in accordance with a relaxation phenomenon. The relaxation breaks down into two processes:

a spin-spin relaxation characterised by a time constant $T_2$, a spin network relaxation characterised by a time constant $T_1$. The intensity of the signal emitted depends, particularly on $T_1$ and $T_2$. The contrast between two different tissues depends therefore on the difference between T1 and T2 of these two tissues.

In MRI, the acquisition sequences of the weighted signals at $T_1$ or at $T_2$ enable information to be obtained on the morphology and the physiology of the organs studied but also on their compositions.

In order that the NMR phenomenon may be observable, the specimen must contain a large number of nuclei possessing a magnetic moment; this is the case in particular of the hydrogen atom $_1H$ of phosphorus $^{31}P$ and of carbon $^{13}C$.

However, MRI runs up against a problem of sensitivity and of contrast. Paramagnetic agents enable this contrast to be increased: in fact, they modify the T1 and T2 of the nuclei of the tissues where they are accumulated and hence the intensity of the signal emitted by these tissues. Besides the anatomical information, paramagnetic contrast agents give also functional information on the tissues wherein they accumulate. They are hence useful for medical diagnosis.

Complexes of chelates and paramagnetic metals are the contrast agents most frequently employed in NMR imaging in the field of medical diagnosis.

The Schering AG Company has described in U.S. Pat. No. 4,647,447 the preparation and use in imaging of NMR contrast agents, and particularly Gd (DTPA)$^2$— (Gadolinium diethylene-triamine pentaacetic acid). This complex has the advantage of being very stable, of low toxicity and well tolerated. On the other hand, it does not show any affinity or any particular target organ of the organism. It is excreted through the urinary path and may be used, particularly, for renal examinations.

Among conventional contrast agents, may also be mentioned super paramagnetic colloids of the dextran-iron oxide type. These colloids are rapidly captured by the reticulo-endothelial system thus enabling the diagnosis at the hepatic and spleen level.

Until now, no soluble and injectable paramagnetic chelate has been described as an NMR contrast agent for use in imaging of the liver. The purpose of the present invention is to propose a contrast agent of the paramagnetic chelate type soluble in aqueous solution which can be administered parenterally, for example by intravenous injection, so as to obtain a contrast effect in NMR imaging of a specific organ, notably the liver. More precisely, it is an object of the present invention to provide a contrast agent which, after administration at low dose, leads to a specific increase in the relaxation of the proton of the water in a particular organ without interfering with other organs and without causing side effects.

It is another object of the invention to provide a contrast agent which has both high stability, low toxicity, that is to say physiologically tolerable on the one hand, and that on the other hand it has properties of relaxivity and osmolarity which are satisfactory for good constrast imaging.

GENERAL DESCRIPTION OF THE INVENTION

Accordingly, the present invention provides a constrast agent for NMR imaging constituted by a complex between a chelating agent and cations of paramagnetic metals, characterised in that said complex corresponds to the formula I:

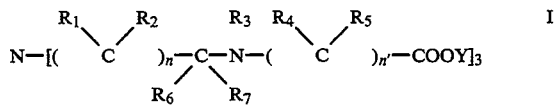

or a physiologically acceptable salt of this complex, in which formula n and n' represent identical or different whole numbers from 1 to 4 n and n' ($R_1$, $R_2$) and ($R_4$, $R_5$) are respectively identical or different from one another, $R_3$, $R_6$ and $R_7$ are selected from among H, a halogen, alkyl alkoxy aryl alkenyl cycloalkyl arylalkyl groups possibly substituted by alkoxy halogen, alkyl, nitrile, nitro or amino groups;

C ($R_6$, $R_7$) can in addition represent C=O;

the three substituents Y are identical or different and represent H or an ionic equivalent of divalent or trivalent paramagnetic metal cation or equivalent of a physiologically acceptable cation derived from an inorganic or organic base, with the condition that at least two of the substituents Y represent ionic equivalents of cations or paramagnetic metals.

These complexes may be neutral or ionic as a function of the respective charges of the chelating agent and of the cation of the complex metal.

When the acid hydrogen atoms of the acid functions of the chelating agent are not all replaced by a paramagnetic ion, it is good, to increase the solubility of he complex, to replace the hydrogen atoms remaining by physiologically inoffensive cations from the physiological point of view derived from inorganic and/or organic bases, particularly amino acid.

The presentation of the complex in salt form is generally required to increase the solubility of the complex in the aqueous phase.

According to the present invention, the alkyl alkoxy groups are radicals of $C_1$ to $C_7$ preferably $C_1$ to $C_4$. There may be mentioned in particular agents for which $R_1$ to $R_5$ represent H, a halogen and an alkyl at $C_1$-$C_4$ possibly substituted by one or more halogens.

The contrast agents of the invention are particularly effective when the paramagnetic metal is selected from among divalent or trivalent ions of transition metals or paramagnetic lanthanides.

There may be mentioned more particularly the following ions: $Co^{2+}$, $Mn^{2+}$, $Cu^{2+}$, $Cr^{3+}$, $Fe^{2+}$, $Fe^{3+}$, $Eu^{2+}$, $Gd^{3+}$, $Dy^{3+}$, $Ho^{3+}$.

There may be mentioned more particularly the contrast agents of formula I for which $>C(R_6R_7)$ represents $>C=O$ Advantageously Y represents for the 3 substituents an ionic equivalent of trivalent cation. That is to say that the acid hydrogen atoms of the chelating agent are replaced by a paramagnetic trivalent ionic equivalent.

This is why, in a particular embodiment of the contrast agents according to the invention, the latter have the formula II

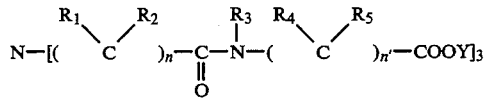

or a physiologically acceptable acid salt of formula III

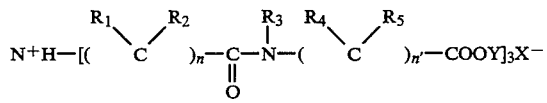

in which $X^-$ is the anion derived from an acid of formula of HX, in which formula Y represents a trivalent paramagnetic metal ionic equivalent n, n', $R_1$, $R_2$, $R_3$, $R_4$, $R_5$ have the previously given meanings.

Preferably the salts obtained with the anions $X^-$ will be used which anions represent $Cl^-$, $Br^-$, $F^-$, $I^-$, $C_nH_{2n+1}COO^-$, $C_6H_5COO^-$, $C_nF_{2n+1}COO^-$, and which are particularly soluble in the aqueous phase.

Among the contrast agents according to the invention, there should be particularly mentioned the agents in which $R_3$=H, as well as those for which $R_1$, $R_2$, $R_4$ and $R_5$=H, as well as those for which n=n--=1.

In the same way, there will be mentioned more particularly the salts obtained with $X^-$=$CF_3COO^-$.

Finally, the contrast agents using the paramagnetic metal $GD^{3+}$ are particularly effective.

By way of example, will be mentioned the contrast agent for the liver in which $R_1$ to $R_6$=H, n=n--=1 and $X^-$=$CF_3COO^-$.

The chelating agents with the peptide structure used in the contrast agents with formula II are novel and consequently, constitute another aspect of the present invention, of which it is also an object to provide compounds corresponding to the formula IV

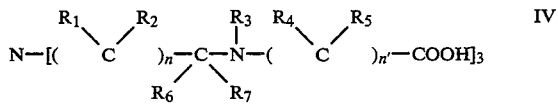

or physiologically acceptable salt of the latter, in which formula n, n--, $R_1$, $R_2$, $R_3$, $R_4$, $R_5$, $R_6$, $R_7$ have the previously given meanings. There will be mentioned in particular the chelating agents for which $>C(R_6R_7)$=$>C=O$.

In a particular embodiment, the chelating agent according to the invention may be solubilized in salt form of formula V

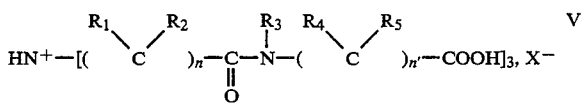

or $X^-$ is derived from an HX acid as previously defined.

These chelating agents of formula IV or V may serve to form complexes with one or more radioactive or not paramagnetic or nor metal cations which can have other uses than the application as a contrast agent NMR.

According to another aspect, it is an object of the present invention to provide a process for the preparation of a contrast agent for NMR imaging according to the invention, characterized in that the chelating agent of formula II in which Y=H or a physiologically acceptable salt such as defined previously is mixed with a compound of said paramagnetic metal at least moderately soluble in water, for example a water soluble paramagnetic salt of which the associated ion is physiologically acceptable, or a carbonate or an oxide, at least slightly soluble, possibly in suspension.

According to another aspect of the present invention, it is an object to provide a method for the preparation of a chelating agent according to the invention, characterized in that a compound of formula

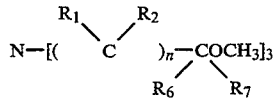

is caused to react with a compound of formula

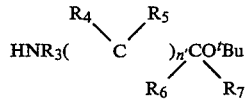

to obtain the compound of formula

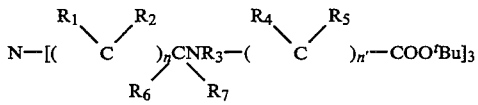

and then the acid functions are deprotected if necessary by reacting the compound with an acid to obtain an ammonium salt.

In general, the complexes, contrasting agents and chelating agents according to the invention, are prepared by methods which employ current reactions.

Preferably, the contrast agents according to the invention are in solution in a solvent serving as a physiologically acceptable vehicle for example water for injection.

Considering that it is preferable for the contrast agent according to the invention to be at a physiological pH, the solution can also contain a buffer.

The administration of contrast agents according to the invention is performed preferably by intravenous injection of a solution containing the paramagnetic chelate in a concentrastion which suffices to confer the contrast effect by NMR imaging desired. In this respect, solutions containing the paramagnetic metal in concentration of 0.2 to 200 mM are suitable.

As an alternative, contrast agents according to the invention may be presented in forms suitable for administration orally, for examples solutions, tablets or capsules.

The contrast agents may conveniently be administered in an amount which fluctuates from $10^{-4}$ to $10^{-1}$ mmoles of paramagnetic metal per kilogram of body weight.

Experiments carried out have shown that the chelates according to the invention were effective relaxation agents which possessed a specificity essentially for the liver, but also for the kidneys as will appear in the examples which follow.

The quality of the images obtained by NMR with the chelates according to the invention is distinctly better than the general standard of the images obtained by NMR published in the literature.

The chelates and contrast agents according to the invention will be further illustrated in the non limiting examples which follow.

BRIEF DESCRIPTION OF THE DRAWINGS

FIG. I represents the image of an organ of a rat by MRI with a Gd contrast agent (MNM-50) before (lefthand column) and after (righthand column) administration of a compound at a dose of 0.1 mmol/kg. The image after administration of the compound Gd (MNM-50) (righthand column) had been taken 10 minutes after injection. The best signals are obtained in the liver and the kidneys.

DESCRIPTION OF THE PREFERRED EMBODIMENTS

Example 1

General Diagram of the Syntheses

The preparation of the contrast agents and of the chelaters according to the invention can be done, for example, according to the scheme below, when $>C(R_6,R_7)=>C=O$.

1) Preparation of:

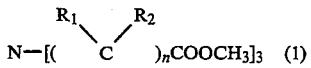

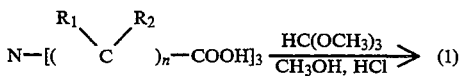

2) Preparation of:

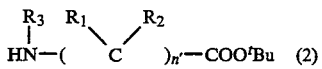

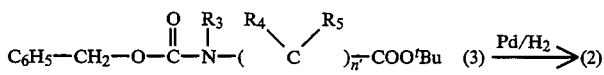

3) Preparation of (3)

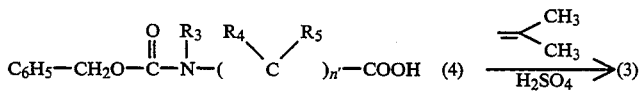

4) Preparation of (4)

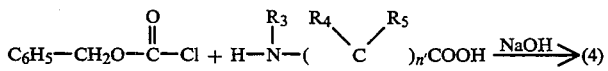

5) Preparation of I-1

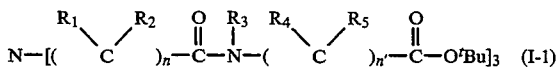

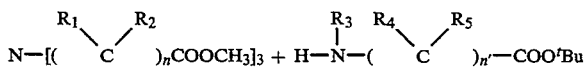

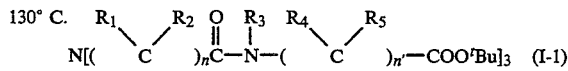

6) Preparation of II-1

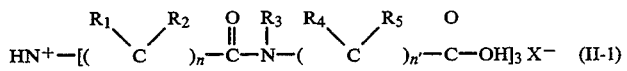

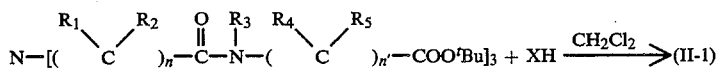

7) Preparation of III-1

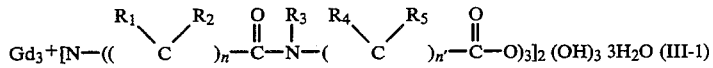

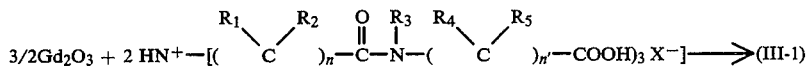

8) Preparation of IV-1

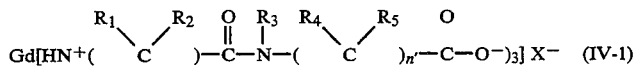

(III-1) + XH ⟶ (IV-1)

Example 2

Preparation of the Intermediate (1) of Formula N(CH₂CONHCH₂COO'Bu)₃

1) Preparation of N(CH₂COOCH₃)₃ (1)

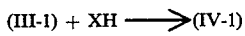

N(CH₂COOCH₃)₃   (1)

To a mixture under stirring of nitrilotriacetic acid [38.2 g; 0.2 moles] and trimethyl orthoformate [84.8 g and 0.8 moles] in methanol [160 ml], is added a gaseous hydrochloric acid [preparation from 30 ml of HCl 12M and 30 ml of H₂SO₄ 36N] at room temperature. When the mixture becomes homogeneous, the reaction is maintained at 65° C. for 12 hours and then at room temperature for 3 days. The solution is brought to pH 10 by the addition of a sodium hydroxide solution in methanol. After concentration under vacuum, the residue is purified by chromatography on a silica gel column with ethyl acetate as eluant. the trimethylnitriloacetate is obtained in the form of a colorless liquid [40 g; yield 90%].

Spectroscopic data IR: 1735 cm−1; 1H NMR (360 MHz, CDCl3); 3.72 (3H, s), 3166 (2 H, s) ppm.

2) Preparation of N-benzyloxycarbonylglycine

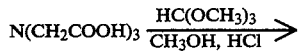

In a glycine solution [15 g; 0.2 moles] in aqueous sodium hydroxide [100 ml of 2N solution] well stirred and cooled in ice, were added to benzyl chlorocarbonate [37.4 g; 0.12 moles] and 2N sodium hydroxide [110 ml] were added in 5 portions at a speed such that the temperature of the mixture was kept below 10 ° C.

Then, the mixture was stirred at room temperature for 18 hours.

After extraction of the mixture with ether [4 times with 100 ml each time] ether was removed from the aqueous phase by bubbling of nitrogen. The solution was then solidified to pH 3 with hydrochloric acid [44 ml of 5M HC] after which an oil separates and slowly solidifies. The solid was filtered, washed with water and dried under vacuum over phosphorus pentoxide, giving colorless N-benzyloxycarbonylglycine 38 g; yield 9 l].

Spectroscopic data, NMR ¹H(360 MHz, CDCl3): 7.35 (5H), 5.25 (1H,br), 5115 (2H, s), 4.05 (2H) ppm.

3) Preparation of terbutyl ester and N-benzyloxycarbonylglycine

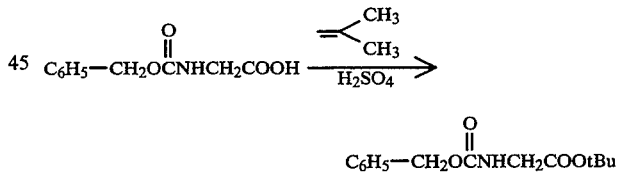

To a solution of N-benzyloxycarbonylglycine [24 g; 0.12 moles] in dichloromethane [240 ml], concentrated sulfuric acid was added 1.5 ml]. The isobutylene obtained from treatment of tert-butanol [110 ml] and by 85% phosphoric acid [40 ml] at 110° C. followed by a trap at −78° C., is led into the reaction mixture with stirring. The closed container was stirred for 3 hours at room temperature.

The solution was washed with an aqueous solution of sodium carbonate [200 ml containing 15 g], with water [3 times 10 ml each time] and dried over anhydrous magnesium sulfate. After filtration, the solution was concentrated under vacuum to give the tert-butyl ester and N-benzyloxycarbonylglycine in the form of a colorless liquid [27.5; yield 91%].

Spectroscopic data NMR 1H (360 MHz, CDCl3): 7.35 (5H), 5.20 (1H, br), 5.12 (2H, s), 3.87 (2H,d) 1.44 (9H, s) ppm.

4) Preparation of tert-butyl ester and glycine

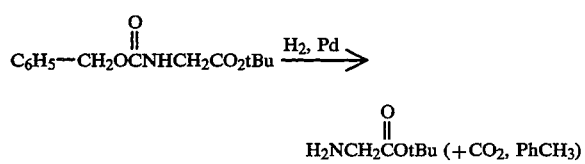

A well stirred suspension of tert-butylester [27.5 g; 0.104 moles] and of 10% of Pd-C [2 g] in anhydrous methanol [150 ml] is treated with hydrogen for 12 hours. After removal of the catalyst by filtration, the filtrate was concentrated under vacuum. The residue was taken up again with ether [150 ml], washed with 10% aqueous sodium carbonate [2 times 50 ml each time] and dried over anhydrous magnesium sulfate. After filtration and concentration under vacuum, the tert-butyl ester of glycine was obtained in the form of a colorless liquid [9.1 g; 67% yield].

Spectroscopic data, NMR $^1$H (360 MHz, CDCl$_3$): 3.30 (2H, s), 1.45 (9H,s) ppm.

5 Preparation of N(CH$_2$CONHCH$_2$COO$^t$Bu)$_3$

A mixture with stirring of tert-butyl ester of glycine [1.1 g; 9 mmoles] and of trimethyl ester of nitrilotriacetic acid [0.58 g; 215 mmoles] was heated to 130° C. for 7 hours. The resultant solid was purified by chromatography on silica gel column using 5% methanol in dichloromethane as eluant to give the desired triester in the form of a clear yellow solid [0.82 g; 63%]. A subsequent purification was carried out by recrystallisation from methylene-hexane chloride (m.p. 145° C).

Spectroscopic data, IR: 1740, 1680, 1645, 1530, 1155 cm$-1$; NMR 1H (360 MHz, CDCl3): 7.75 (eH, t), 3.96 (6H, s), 3.38 (6H, s), 1.45 (27H, s) ppm; MS: m/z at 530 (M+, 15), 457 (15), 399 (15), 287 (25), 260 (100), 246 (15), 145 (45), 57 (45).

Example 3

Preparation of the Intermediate (II-1)

[HN$^+$(CH$_2$CONHCH$_2$COOH)$_3$].CF$_3$COO$^-$ (compound MNM-50) (II-1)

To a solution of N(CH$_2$CONHCH$_2$COOBu$^t$)$_3$, [I, 0.5 g, 0.93 mmoles] in CH$_2$Cl$_2$ [24 ml] was added CF$_3$COOH [24 ml]. The reaction mixture was stirred at 20° C. for 18 hours. The volatile materials were removed by evaporation under vacuum, then diethyl ether was added to the residue to precipate a white solid. The white solid was collected by filtration, washed with ether [5 times 5 ml] and dried under vacuum.

Yield=0.38 g, 86%

Spectroscopic data: NMR $^1$H (d$^6$DMSO)=3.58 singlet (2HN-CH2; 3.85 doublet (2H) NH-CH2 (3jH-H=5.8 Hz); 8.58 singlet wide (1H), NH.

NMR $^{19}$(F($^1$H)) (DMSO)= −74.5 ppm singlet.

|    | Microanalyses: Found | Theoretical |
|----|---------------------|-------------|
| C; | 35.43               | 35.30       |
| H; | 4.32                | 4.02        |
| N; | 11.08               | 11.76       |

Example 4

Preparation of Intermediate (III-1)

Gd$_3$[N(CH$_2$CONHCH$_2$COO)$^-$$_3$]$_2$(OH)$_3$3H2O (III-1)

To a suspension of Gd$_2$O$_3$ [0.256 g, 0.7 mmoles] in water [150 ml] was added the compound MNM-50 [II, 0.57 g, 1.57 mmoles].

The reaction mixture was first of all stirred at 80° C. for 1 hour then the temperature raised to 100° C. and stirring was continued for 4 hours. After cooling, a white solid was filtered and washed with water, ethanol and pentane then dried under vacuum.

Yield: 0.5 g, 58%

|    | Microanalyses: Found | Theoretical |
|----|---------------------|-------------|
| C: | 23.7                | 22.3        |
| H: | 3.8                 | 3.01        |
| N: | 8.9                 | 8.7         |

Example 5

Preparation of the Complex Salt

Gd$^3$[HN$^+$(CH$_2$CONHCH$_2$COO$^-$)$_3$CF$_3$COO$^-$½CF$_3$COOH.2H$_2$O (IV-1) (Gd MNM-50)

Some Gd$^3$[N(CH$_2$CONHCH$_2$COO$^-$)$_3$]$_2$2(OH)$_3$3-H$_2$O (III, 0.4 g, 0.72 mmoles) was disolved in CF$_3$COOH [0.1M, 100 ml] at 20° C.; all the insoluble products were removed by filtration then the filtrate was stirred at 70° C. for 1 hour, then at 20° C. for 18 hours. The volatile materials were removed by evaporation under vacuum. The oily residue was washed with diethyl ether to give a white solid which was isolated by filtration, washed with diethyl ether (10 times 4 ml) and dried under vacuum.

Yield: 0.43 g; 83%

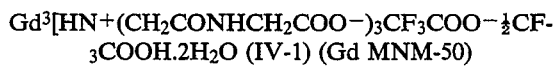

|    | Microanalyses: Found | Theoretical |
|----|---------------------|-------------|
| C: | 24.26               | 24.9        |
| H: | 2.68                | 2.85        |
| N: | 7.13                | 7.74        |
| F: | 11.37               | 11.80       |

Example 6

Results

The relaxation time T1 was determined on a Brucher Minispec at 20 MHz, or Jeol at 100 MHz at 37° C.

The osmolarity was measured with an osmometer [Wescor - Inc, 5100B] at 21° C. and at a concentration of 0.05M.

Studies were carried out on tissues excised in the following manner. Selected organs such as the liver, spleen, the kidneys, blood samples were collected on female Wistar rats which were sacrificed 15 minutes after intravenous injection of the contrast agent [IV] at a dose of 0.1 mmoles/kg.

The relaxivity of the compound according to the invention of formula IV [example 5][below Gd MNM-50] was measured on the minispec 20 MHz. The results are shown in the following table 1.

TABLE 1

| Medium | T1 msec | R1 (mM−1sec)−1 |
|---|---|---|
| Water | 86* | 11.6 |
| Human serum albuin (2.5 mg/100 ml) | 42 | 23.8 |
| Acetate buffer pH = 5.0.1M | 90 | 11.1 |

*At 100 MHz, $T_1 = 100$ msec, $R_1 = 10$ $(mM^{-1} sec)^{-1}$ by comparison: with the complex $Gd(DTPA)^{2-}$ $T_1 = 180$ msec, $R_1 = 5.5$ $(mM^{-1}sec)^{-1}$ in water The osmolarity of the compound Gd(MNM-50) was measured at 21° C. at a concentration of 0.05M in a physiological solution [NaCl 0.9%].

Gd(MNM-50) has an osmolarity of 35 mosmol/kg. This result is to be compared with the osmolarity obtained with $Gd(DTPA)^{2-}$ whose osmolarity is equal to 398 mosmol/kg, 0.2 ml Magnevist diluted to 2 ml with saline solution.

There was therefore noted a much greater relaxivity with the compound Gd(MNM-50) according to the invention than with the complex $Gd(DTPA)^{2-}$, in the same way as an osmolarity distinctly weaker in favor of Gd(MNM50).

Table 2 below gives the measurements in vitro of $T_1$ on tissues excised from rats for an injected dose of 0.1 mmol/kg of Gd(MNM-50) or Gd $(DTPA)^{2-}$.

TABLE 2

| Compound Organs | Gd(MNM-50) msec | Gd(DTPA)$^{2-}$ msec | Control msec |
|---|---|---|---|
| Liver | 139 | 597 | 742 |
| Blood | 138 | 782 | 1380 |
| Spleen | 330 | 805 | 973 |
| Kidneys | 722 | 237 | 1230 |

FIG. 1 represents a photograph of the tissues of the rats before and after administration of the compound Gd(MNM-50) at a dose of 0.1 mmol/kg. The image after administration of the Gd(MNM-50) [righthand column] was taken 10 minutes after the injection. As can be seen in the figure, important contrasts are obtained between the liver and the kidneys, on the one hand and the other tissues, on the other hand. The contrast agent Gd(MNM50) is fixed moreover in quite a remarkable manner in the liver.

We claim:

1. A complex between a chelating agent and a paramagnetic metal cation, having the formula:

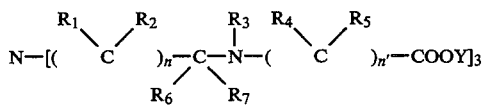

or a physiologically acceptable salt of this complex, wherein
n and n' are the same or different and are selected from the group consisting of whole numbers of from 1 to 4;
each $R_1$, $R_2$, $R_4$ and $R_5$ are the same or different and are selected from the group consisting of H, halogen and $C_{1-4}$ alkyl, the $C_{1-4}$ alkyl being optionally substituted by halogen;
$R_3$ is hydrogen;
$>C(R_6, R_7)$ is $>C=O$;
the three substituents Y are the same or different and represent H or the cation ionic equivalent of a trivalent paramagnetic metal cation or the anionic equivalent of a physiologically acceptable cation derived from an inorganic or organic base, at least two of the substituents Y representing ionic equivalents of cations of paramagnetic metals.

2. A complex according to claim 1, wherein the paramagnetic metal is selected from among divalent or trivalent ions of transition metals and lanthanides.

3. A complex according to claim 2, wherein the paramagnetic metal is selected from among $Co^{2+}$, $Mn^{2+}$, $Cu^{2+}$, $Cr^{3+}$, $Fe^{2+}$, $Fe^{3+}$, $Eu^{2+}$, $Gd^{3+}$, $Dy^{3+}$ and $Ho^{3+}$.

4. A complex according to claim 1, having the formula II

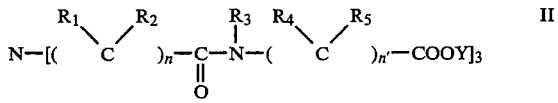

or a physiologically acceptable acid salt of formula

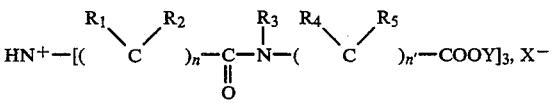

in which $X^-$ is the anion derived from an acid of formula HX, in which formulae
Y represents an ionic equivalent of a trivalent paramagnetic metal;
n, n', $R_1$, $R_2$, $R_3$, $R_4$ and $R_5$ have the previously given meanings.

5. A complex according to claim 4 wherein $X^-$ represents $Cl^-$, $Br^-$, $F^-$, $I^-$, $C_nH_{2n+1}COO^-$, $C_6H_5COO^-$, or $C_nF_{2n+1}COO^-$.

6. A complex according to claim 1, wherein $R_1=R_2=R_4=R_5=H$.

7. A complex according to claim 1, wherein $n=n'=1$.

8. A complex according to claim 4, wherein $X^-=CF_3COO^-$.

9. A complex according to claim 1, wherein the paramagnetic metal is the Gadolinium $Gd^{3+}$ ion.

10. A contrast agent for NMR imaging comprising a complex according to claim 1 and a physiologically acceptable carrier.

11. A chelating agent with a peptide structure which can form complexes with metals and has the formula:

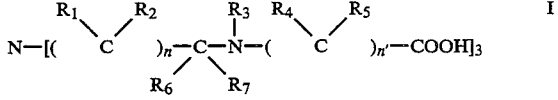

or a physiologically acceptable salt thereof, wherein
n and n' are the same or different and are selected from the group consisting of whole numbers from 1 to 4;
each $R_1$, $R_2$, $R_4$ and $R_5$ are the same or different and are selected from the group consisting of H, halogen and $C_{1-4}$ alkyl, the $C_{1-4}$ alkyl being optionally substituted by halogen;
$R_3$ is hydrogen; and $>C(R_6, R_7)$ is $>C=O$.

12. Chelating agent according to claim 11, said agent having the formula

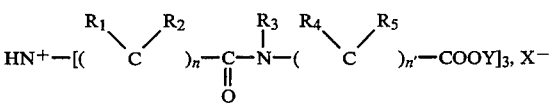

wherein $X^-$ is derived from an HX acid.

* * * * *